US008123698B2

(12) United States Patent
Mark

(10) Patent No.: US 8,123,698 B2
(45) Date of Patent: Feb. 28, 2012

(54) SYSTEM AND METHOD FOR MINIMALLY INVASIVE DISEASE THERAPY

(75) Inventor: Joseph L. Mark, Indianapolis, IN (US)

(73) Assignee: Suros Surgical Systems, Inc., Indianapolis, IN (US)

(*) Notice: Subject to any disclaimer, the term of this patent is extended or adjusted under 35 U.S.C. 154(b) by 686 days.

(21) Appl. No.: 11/237,110

(22) Filed: Sep. 28, 2005

(65) Prior Publication Data
US 2007/0083129 A1 Apr. 12, 2007

Related U.S. Application Data

(63) Continuation-in-part of application No. 10/649,068, filed on Aug. 27, 2003, now Pat. No. 7,347,829.

(60) Provisional application No. 60/416,755, filed on Oct. 7, 2002.

(51) Int. Cl.
A61B 10/00 (2006.01)
A61B 17/32 (2006.01)

(52) U.S. Cl. ........ 600/567; 600/563; 600/564; 600/566; 606/170; 606/172

(58) Field of Classification Search .................. 600/566, 600/563, 564, 567; 606/37, 170, 172
See application file for complete search history.

(56) References Cited

U.S. PATENT DOCUMENTS

| 4,649,151 A * | 3/1987 | Dougherty et al. ........... 514/410 |
|---|---|---|
| 5,199,441 A | 4/1993 | Hogle |
| 5,279,542 A | 1/1994 | Wilk |
| 5,817,048 A | 10/1998 | Lawandy |
| 5,913,813 A | 6/1999 | Williams et al. |
| 6,142,955 A | 11/2000 | Farascioni et al. |
| 6,296,608 B1 | 10/2001 | Daniels et al. |
| 6,315,737 B1 | 11/2001 | Skinner |
| 6,371,904 B1 | 4/2002 | Sirimanne et al. |
| 6,413,204 B1 | 7/2002 | Winkler et al. |
| 6,440,138 B1 * | 8/2002 | Reiley et al. ................... 606/79 |
| 6,482,142 B1 | 11/2002 | Winkler et al. |
| 6,494,844 B1 | 12/2002 | Van Bladel et al. |
| 6,558,382 B2 * | 5/2003 | Jahns et al. .................... 606/41 |
| 6,638,235 B2 | 10/2003 | Miller et al. |
| 6,676,658 B2 | 1/2004 | Burbank et al. |
| 6,752,805 B2 * | 6/2004 | Maguire et al. ................ 606/41 |
| 6,758,824 B1 | 7/2004 | Miller et al. |

(Continued)

FOREIGN PATENT DOCUMENTS

EP 0161606 11/1985

(Continued)

OTHER PUBLICATIONS

Reuters Heatlh publication entitled "Contrast mammography shows promise in cancer detection." author David Douglas.

(Continued)

Primary Examiner — Max Hindenburg
Assistant Examiner — Sean Dougherty
(74) Attorney, Agent, or Firm — Vista IP Law Group LLP

(57) ABSTRACT

A system for treating a lesion site of a patient is disclosed. The system includes a cannula having a lumen, a conduit in communication with said lumen, an introducer stylet removably disposed within said cannula, a resecting device selectively insertable within said cannula, and an adjuvant treatment device selectively insertable within said cannula.

20 Claims, 12 Drawing Sheets

U.S. PATENT DOCUMENTS

| | | | |
|---|---|---|---|
| 6,790,636 B1 | 9/2004 | Star et al. | |
| 6,923,754 B2 | 8/2005 | Lubock | |
| 6,945,942 B2 | 9/2005 | Van Bladel et al. | |
| 6,955,641 B2 | 10/2005 | Lubock | |
| 6,979,290 B2 | 12/2005 | Mourlas et al. | |
| 7,066,893 B2 | 6/2006 | Hibner et al. | |
| 7,150,712 B2* | 12/2006 | Buehlmann et al. | 600/114 |
| 7,179,232 B2 | 2/2007 | Sutton et al. | |
| 7,338,430 B2* | 3/2008 | Lim et al. | 600/7 |
| 7,347,829 B2 | 3/2008 | Mark et al. | |
| 7,517,310 B2* | 4/2009 | Lubock et al. | 600/3 |
| 7,618,362 B2 | 11/2009 | DiCarlo et al. | |
| 7,740,597 B2 | 6/2010 | Cicenas et al. | |
| 2002/0029007 A1 | 3/2002 | Bryan et al. | |
| 2002/0029060 A1* | 3/2002 | Hogendijk | 606/185 |
| 2002/0161298 A1 | 10/2002 | Burbank et al. | |
| 2003/0083542 A1* | 5/2003 | Alferness et al. | 600/37 |
| 2003/0093007 A1* | 5/2003 | Wood | 600/564 |
| 2003/0097079 A1 | 5/2003 | Garcia | |
| 2003/0130575 A1 | 7/2003 | Desai | |
| 2003/0149327 A1* | 8/2003 | Chin et al. | 600/1 |
| 2003/0212373 A1 | 11/2003 | Hall et al. | |
| 2004/0019299 A1 | 1/2004 | Ritchart et al. | |
| 2004/0024304 A1* | 2/2004 | Foerster et al. | 600/407 |
| 2004/0077938 A1* | 4/2004 | Mark et al. | 600/411 |
| 2004/0077972 A1 | 4/2004 | Tsonton et al. | |
| 2004/0153003 A1 | 8/2004 | Cicenas et al. | |
| 2004/0267154 A1 | 12/2004 | Sutton et al. | |
| 2005/0059884 A1 | 3/2005 | Krag | |
| 2005/0165329 A1 | 7/2005 | Taylor et al. | |
| 2005/0234336 A1 | 10/2005 | Beckman et al. | |
| 2005/0240074 A1 | 10/2005 | Lubock | |
| 2005/0256508 A1 | 11/2005 | Hall | |
| 2006/0009712 A1* | 1/2006 | Van Bladel et al. | 600/566 |
| 2006/0111605 A1* | 5/2006 | Larsen et al. | 600/1 |
| 2006/0167416 A1 | 7/2006 | Mathis et al. | |
| 2006/0169293 A1 | 8/2006 | Yokoi et al. | |
| 2006/0173296 A1 | 8/2006 | Miller et al. | |
| 2006/0217587 A1 | 9/2006 | DiCarlo et al. | |
| 2006/0260994 A1 | 11/2006 | Mark et al. | |
| 2007/0055282 A1 | 3/2007 | Muschler | |
| 2007/0142725 A1 | 6/2007 | Hardin et al. | |
| 2007/0219460 A1 | 9/2007 | Goldenberg | |
| 2007/0293788 A1 | 12/2007 | Entrekin et al. | |
| 2008/0200834 A1 | 8/2008 | Mark et al. | |

FOREIGN PATENT DOCUMENTS

| | | |
|---|---|---|
| GB | 1252170 | 11/1971 |
| WO | WO-01/82810 | 11/2001 |
| WO | WO2004/043531 | 5/2004 |

OTHER PUBLICATIONS

Aunt Minnie.com publication entitled "TechniScan system completes phase I trials."

MSNBC Heath Publication entitled "Seeds may zap breast cancer." Author Robert Bezell.

Radiology Today—Technology Trends, article entitled "New Use for an Old Technology Applying Tomosynthesis to Mammography." Author Dan Harvey.

Biophontonics International—Imaging article entitled "Optoacoustics Moves Closer to the Clinic." Author Nadya Anscombe.

PCT International Search Report #PCT/IB2006/053504 dated Apr. 2, 2007.

Office Action for U.S. Appl. No. 11/550,209 dated Aug. 4, 2008.

Amendment to Office Office Action for U.S. Appl. No. 11/550,209 dated Oct. 16, 2008.

Office Action Dated Jul. 9, 2008 for U.S. Appl. No. 12/061,344.

Amendment in Response to OA dated Jul. 9, 2008 for U.S. Appl. No. 12/061,344.

Final Office Action dated Jan. 28, 2009 for U.S. Appl. No. 12/061,344.

Final Office Action dated Jan. 28, 2009 for U.S. Appl. No. 11/550,209.

Response to Final Office Action dated Jan. 28, 2009 for U.S. Appl. No. 11/550,209.

Response to Final Office for U.S. Appl. No. 12/061,344 dated Mar. 19, 2009.

Office Action dated Jun. 19, 2009 for U.S. Appl. No. 12/061,344.

Office Action dated Jul. 21, 2009 for U.S. Appl. No. 11/550,209.

Response to Office Action dated Jun. 19, 2009 for U.S. Appl. No. 12/061,344.

Response to Office Action dated Jul. 21, 2009 for U.S. Appl. No. 11/550,209.

Final Office Action dated Jan. 19, 2010 for U.S. Appl. No. 12/061,344.

Response to Final Office Action dated Feb. 3, 2010 for U.S. Appl. No. 11/550,209.

Non-Final Office Action dated Apr. 12, 2010 for U.S. Appl. No. 12/061,344.

Response to Non-Final Office Action dated Apr. 12, 2010 for U.S. Appl. No. 12/061,344.

PCT International Search Report for PCT/IB07/54229 dated Jul. 9, 2010.

Final Office Action dated Feb. 3, 2010 for U.S. Appl. No. 11/550,209.

Response to Final Office Action Jan. 19, 2010 for U.S. Appl. No. 12/061,344.

Final Office Action dated Sep. 23, 2010 for U.S. Appl. No. 12/061,344.

Non-Final Office Action dated Oct. 25, 2010 for U.S. Appl. No. 12/061,195.

Response to Final Office Action dated Sep. 23, 2010 for U.S. Appl. No. 12/061,344.

Response to Non-Final Office Action dated Oct. 25, 2010 for U.S. Appl. No. 12/061,195.

Final Office Action dated Feb. 8, 2011 for U.S. Appl. No. 11/550,209.

Response to Non-Final Office Action dated Feb. 8, 2011 for U.S. Appl. No. 11/550,209.

Non-Final Office Action dated Apr. 29, 2011 for U.S. Appl. No. 11/550,209.

Final Office Action dated Mar. 22, 2011 for U.S. Appl. No. 12/061,195.

Response to Final Office Action dated Mar. 22, 2011 for U.S. Appl. No. 12/061,195.

Response to Non-Final Office Action dated Apr. 29, 2011 for U.S. Appl. No. 11/550,209.

* cited by examiner

SYSTEM AND METHOD FOR MINIMALLY INVASIVE DISEASE THERAPY

CROSS REFERENCE TO RELATED APPLICATIONS

This application is a Continuation-in-Part application of U.S. patent application Ser. No. 10/649,068, filed on Aug. 27, 2003, now issued as U.S. Pat. No. 7,347,829, which application claims priority to U.S. Provisional Application Ser. No. 60/416,755, filed on Oct. 7, 2002.

BACKGROUND

1. Field of the Invention

The present invention relates generally to a surgical system and method for removing and treating diseased tissue and more particularly to a minimally invasive system and method for removing diseased tissue and creating a margin around an excised area.

2. Description of the Related Art

Surgical cancer treatments have advanced to two primary stages. A first stage removes the cancerous tissue by resecting the tissue from the body. The goal of the first stage is to remove all cancerous cells from a target area. However, unless a large portion of healthy tissue is also resected, a possibility exists that some cancerous cells remain near the resection site.

A second stage typically involves a broad-based radiation therapy to the cancerous region. The radiation therapy is necessary to destroy any cancerous tissue that may have remained in the targeted area after resection. However, broad-based radiation therapy requires multiple exposures to high doses of radiation. Such exposure results in undesirable side effects and the exposure may not be limited to the tissues that surrounded the resected tissue. Further, a full course of treatment may require six weeks of individual treatments that result in frequent visits to a hospital or treatment suite.

Accordingly, an improved treatment method is desired that improves treatment effectiveness, reduces side effects, reduces treatment time, avoids widespread exposure to radiation, and is verifiable using medical imaging techniques. Additionally, an improved treatment method is desired that may be used with multiple imaging modalities, these modalities may include Magnetic Resonance Imaging (MRI), ultrasound, and x-ray Computed Tomography (CT).

SUMMARY

A system for treating a lesion site of a patient is disclosed. In one embodiment the system includes a cannula having a lumen, a conduit in communication with the lumen, an introducer stylet removably disposed within the cannula, a resecting device selectively insertable within the cannula, and an adjuvant treatment device selectively insertable within the cannula.

A method of treating a lesion site of a patient is also disclosed. The method includes the steps of inserting an introducer stylet having an outer cannula disposed thereon into a patient's body creating a pathway to a lesion site, removing the introducer stylet from the patient's body leaving behind the outer cannula. The method may further include inserting a resection device into the patient's body through the outer cannula and removing tissue from the lesion site, removing the resection device from the patient's body leaving behind the outer cannula. Further, the method may include inserting an adjuvant therapy device into the patient's body through the outer cannula, and treating the lesion site using the adjuvant therapy device.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION

Figure 1:
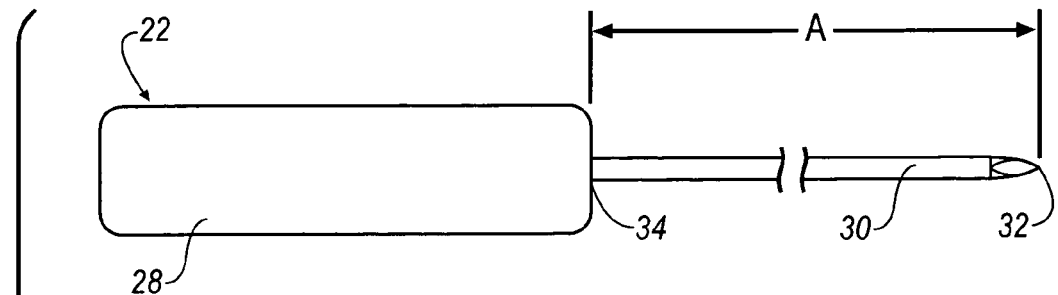
FIG. 1 is a side view of an introducer stylet in accordance with an embodiment of the present invention.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Figure 2:
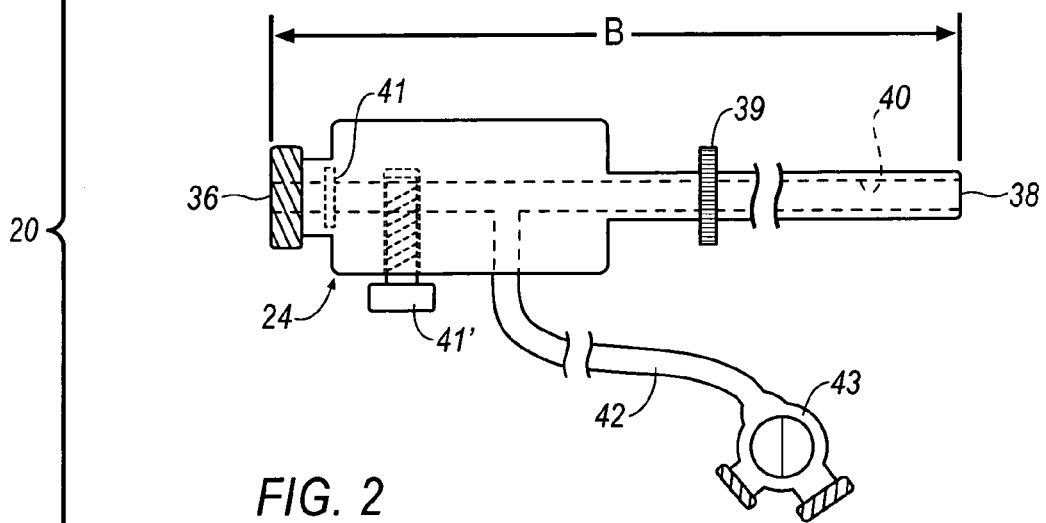
FIG. 2 is a side view of an outer cannula and fluid conduit in accordance with the embodiment of FIG. 1.
Figure 3:
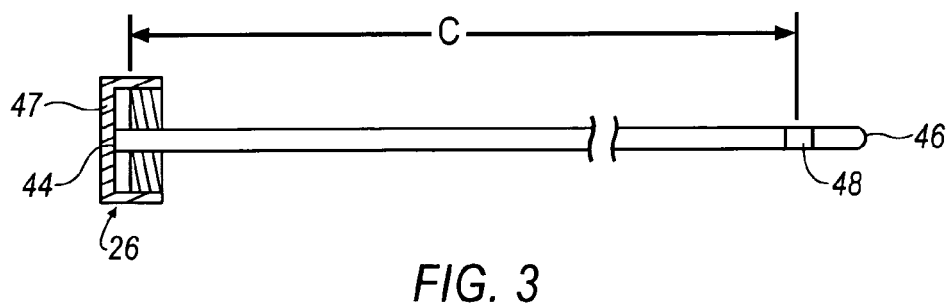
FIG. 3 is a side view of a target confirmation device in accordance with the embodiment of FIG. 1.

Referring to FIGS. 1-3, a medical system 20 is shown that includes an introducer stylet 22, an outer cannula 24 and a target confirmation device 26. As will be described in detail, system 20 is particularly, but not necessarily, suited for use in biopsy procedures that identify the target biopsy site using Magnetic Resonance Imaging (MRI) or a comparable medical imaging modality. A system similar to system 20 can be seen by way of example in pending U.S. patent application, Ser. No. 10/649,068, which is owned by the assignee of the present invention and is incorporated herein by reference in its entirety.

In one embodiment, introducer stylet 22 includes a handle 28 and a stylet 30 having a distal end 32 and a proximal end 34 connected to handle 28. Handle 28 may be made of a medical grade resin or other MRI compatible material. Stylet 30 may also be made of an MRI compatible, medical grade material, such as 316 stainless steel or inconel 625.

In one particular configuration, distal end 32 of stylet 30 may be provided with a tissue piercing tip, such as a trocar tip, to facilitate penetration of stylet 30 into a patient's tissue. In addition to a trocar tip, it will be appreciated that stylet 30 may include other devices for piercing the patient's tissue, including without limitation, devices that use a laser, radiofrequencies (RF), or ultrasonics to pierce the tissue. The length of stylet 30 is generally denoted by the reference character "A" in FIG. 1.

Referring to FIG. 2, an embodiment of outer cannula 24 is shown. Outer cannula 24 extends from an open proximal end 36 to an open distal end 38, which is separated from proximal end 36 by a distance generally denoted by the reference character "B". Like introducer stylet 30, outer cannula 24 may be made from a medical grade resin or other MRI compatible material. In some configurations, proximal end 36 may include a luer-style fitting or other suitable configuration for interfacing, but not necessarily connecting, outer cannula 24 with target confirmation device 26. A depth limiting member 39, such as, for example, a rubber o-ring, may be moveably disposed on outer cannula 24 to limit the insertion depth of outer cannula 24 into the patient's body.

In one embodiment, outer cannula 24 may also include an inner lumen 40 therethrough, which is open to communication with a fluid conduit 42 for supplying fluids, such as saline and anesthetics, or removing fluids, such as blood, from the patient's body. Fluid conduit 42 communicates with inner lumen 40 via a port in outer cannula 24. In some configurations, outer cannula 24 may include a haemostatic valve, depicted generally as element 41, or a manually operable valve 41' that can be selectively closed to prevent the escape of fluid from proximal end 36. Fluid conduit 42 may also include a directional valve 43 to selectively control the supply and removal of fluid to and from inner lumen 40, respectively.

In FIG. 3, an embodiment of target confirmation device 26 is depicted. Target confirmation device 26 is an elongated member that is sized to fit within inner lumen 40 of outer cannula 24. Target confirmation device 26, which may be made of a medical grade resin or other MRI compatible material, extends from a connecting end 44 to a distal end 46. Connecting end 44 may be configured with a cap 47 that abuts proximal end 36 of outer cannula 24 when target confirmation device 26 is inserted into outer cannula 24. In some configurations, cap 47 may include a luer-style fitting or other suitable feature for interfacing, but not necessarily connecting, target confirmation device 26 with outer cannula 24.

Distal end 46 of target confirmation device 26 may be generally rounded to facilitate entry into the patient's body. In one embodiment, a portion of target confirmation device 26 is configured with a magnetic resonance imaging (MRI) identifiable material, such as inconel 625, titanium or other material with similar magnetic characteristics. In one particular configuration, a targeting band 48 is provided a distance "C" from connecting end 44, as shown in FIG. 3; the distance "C" being measured from the approximate center of targeting band 48 to connecting end 44 (or the inside of cap 47), for example. Targeting band 48 provides a reference point in an MR image relative to the target biopsy tissue.

In another embodiment of target confirmation device 26, the tip of target confirmation device 26 itself may be used to provide the reference point in the MR image, provided the target confirmation device material exhibits a relatively low artifact during MR imaging. As used herein, the term "artifact" describes a material's tendency to distort an MR image. A material exhibiting a relatively high artifact will render the body tissue surrounding the material unreadable in an MR image. Conversely, a material with a relatively low artifact or signal void will allow the material to be readily identified in the MR image and will not significantly distort the MR image of the surrounding tissue.

Figure 3A:
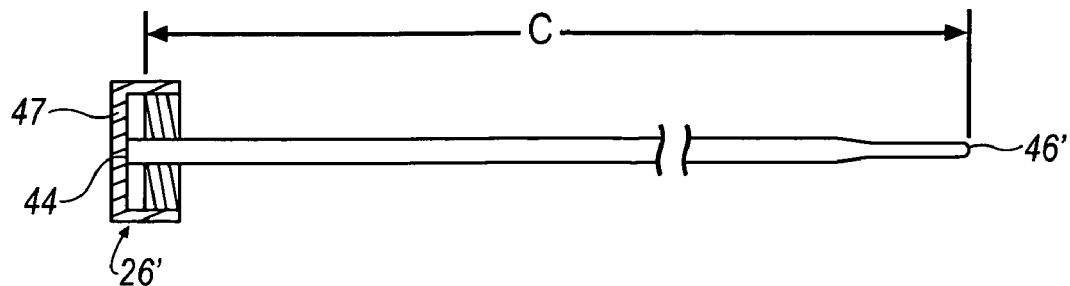
FIG. 3A and 3B are side views of target confirmation devices according to alternate embodiments of the present invention.
Figure 3B:
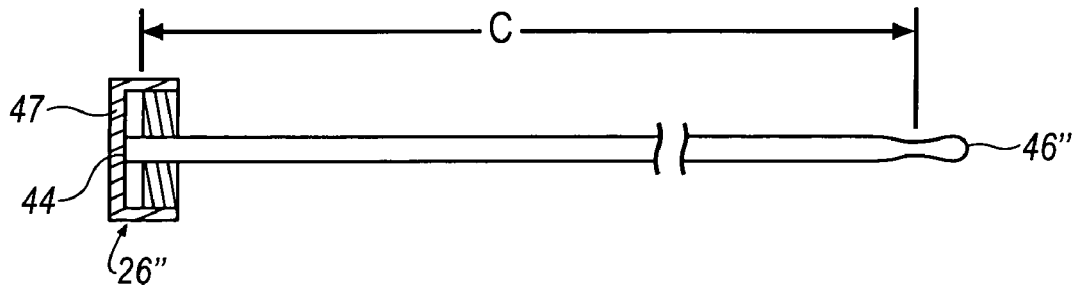

As shown in the embodiments of FIGS. 3A and 3B, distal end 46', 46" of target confirmation device 26', 26" may include a particular shape to help identify the location of target confirmation device 26 relative to the surrounding tissue. In the embodiment of FIG. 3A, a portion of target confirmation device 26' adjacent distal end 46' has a smaller diameter relative to the remaining length. Alternatively, in the embodiment of FIG. 3B, a portion of target confirmation device 26" has a tapered distal end 46" to provide an hour glass like image when viewed under MR. It will be appreciated that the target confirmation devices represented in FIGS. 3, 3A and 3B are not limited to the configurations shown, and that other configurations are with in the scope of the present invention.

In still another embodiment, stylet 30 may function as a target confirmation device. In this embodiment, introducer stylet 22, and more particularly stylet 30, may be made of an MRI compatible material that preferably, but not necessarily, exhibits a relatively low artifact.

Figure 4:
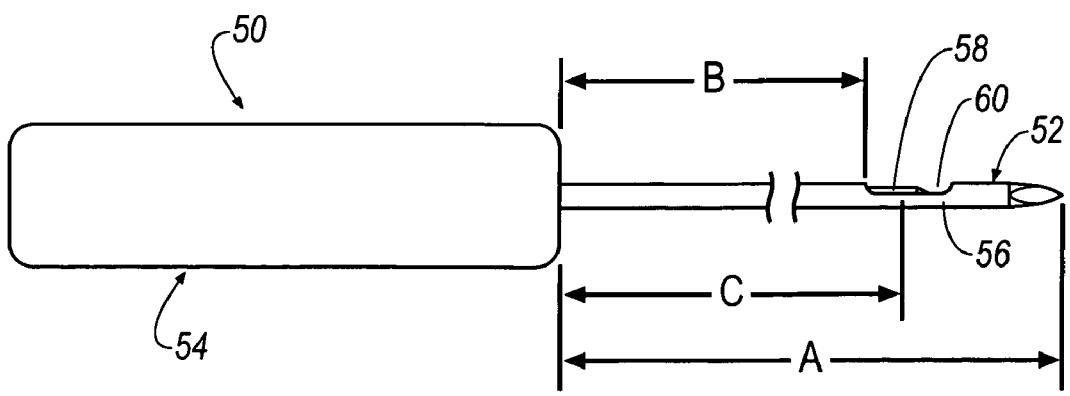
FIG. 4 is a side view of an exemplary biopsy device for use with an introduction system of the present invention.
Figure 5:
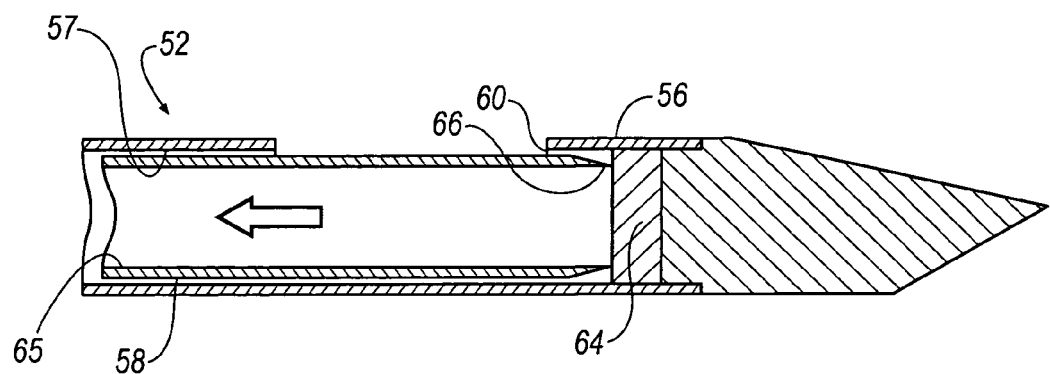
FIG. 5 is a detailed cross sectional view of a cutting element of the biopsy device of FIG. 4.

An exemplary resection apparatus 50, which is suitable for use with system 20 of the present invention, is generally shown in FIG. 4 and in more detail in FIG. 5. Resection apparatus 50 includes a cutting element 52 sized for introduction into a handpiece 54. The exemplary resection apparatus 50 is configured as a "tube-within-a-tube" cutting device. More particularly, cutting element 52 includes an outer cannula 56 having an outer lumen 57 and an inner cannula 58 sized to fit concentrically within the outer lumen. A motor or other motion generating device is provided within handpiece 54 to rotate and/or translate inner cannula 58 within outer cannula 56. A biopsy apparatus similar to resection apparatus 50 can be seen by way of example in pending U.S. patent applications, Ser. Nos. 09/707,022 and 09/864,031, which are owned by the assignee of the present invention and are incorporated herein by reference in their entirety.

One embodiment of a working end of cutting element 52 is depicted in FIG. 5. In the illustrated embodiment, outer cannula 56 defines a tissue-receiving opening 60, which communicates with outer lumen 57. The working end of cutting element 52 may further include a cutting board 64 that is disposed within outer lumen 57 at the distal end of outer cannula 56. Inner cannula 58 defines an inner lumen 65 that is hollow along its entire length to provide for aspiration of the biopsy sample (tissue). Inner cannula 58 terminates in a cutting edge 66 that may be formed by an inwardly beveled surface having a razor-sharp edge.

Figure 6:
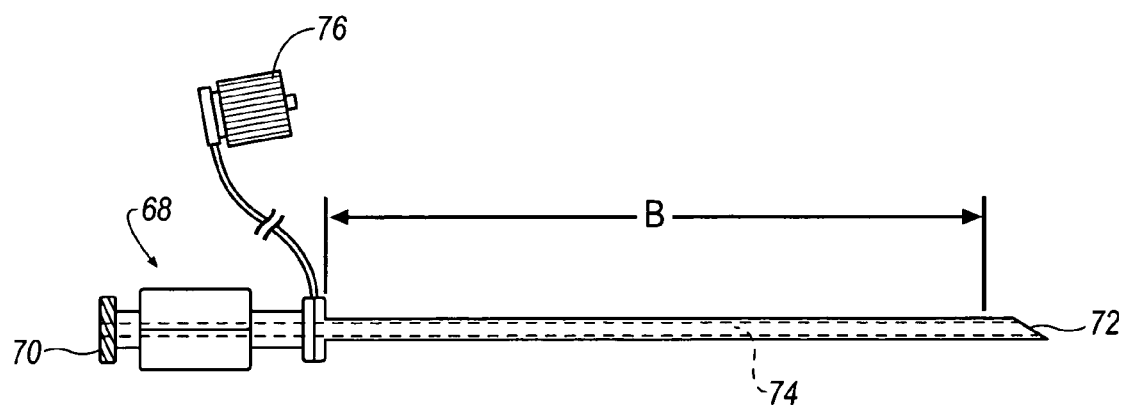
FIG. 6 is a side view of an aspiration wand suitable for insertion into the outer cannula of FIG. 2.

Referring to FIG. 6, a wand 68 is shown that can be inserted into outer cannula 24 after resection apparatus 50 has been removed, or at any time outer cannula 24 is free of obstruction. In one embodiment, wand 68 extends from a connecting end 70 to an insertion end 72 and includes a lumen 74 that extends from connecting end 70 to insertion end 72. Connecting end 70 may include a luer interface or other suitable fitting for connecting wand 68 to a vacuum source (not shown) or a fluid source (not shown). Wand 68 may also include a cap 76 that can be placed onto connecting end 70 to inhibit fluid leakage when wand 68 is inserted into the patient. The haemostatic valve 41 in outer cannula 24 seals against wand 68, as it does against target confirmation device 26 and resection apparatus 50, when inserted into outer cannula 24. Additionally, the outside diameter of wand 68 is preferably less than the inside diameter of inner lumen 40 to allow the passage of fluids through fluid conduit 42 to pass into or out of the patient's body. When cap 76 is removed and wand 68 is connected to a vacuum source, fluids, such as blood and saline, can be aspirated from the biopsy site or, conversely, when connected to a fluid source, fluids can be delivered to the biopsy site.

Figure 7:
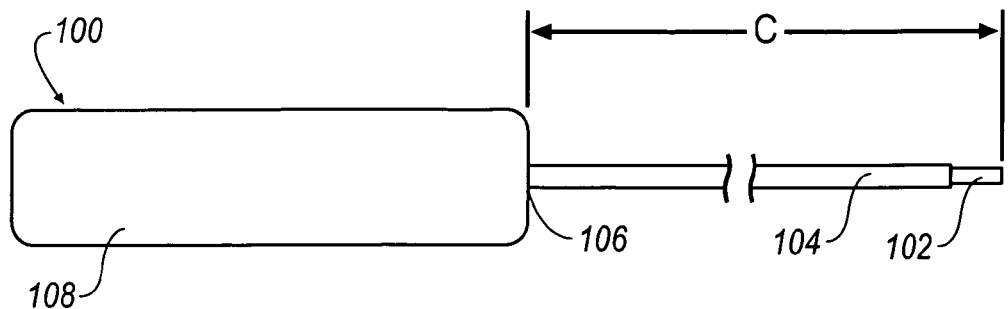
FIG. 7 is a side view of a treatment device wand suitable for insertion into the outer cannula of FIG. 2.

Referring to FIG. 7, a treatment device 100 is shown that can be inserted into outer cannula 24. In one embodiment, treatment device 100 includes a treatment tip 102 sized for introduction into the patient's body, a treatment shaft 104 having a proximal end 106, and a treatment handpiece 108. A fluid system, electrical system, or other supporting elements may be attached to, or operate in cooperation with, treatment handpiece 108 in order to effectuate an adjuvant treatment at treatment tip 102 (to be explained in further detail with respect to FIGS. 8-11).

Figure 8:
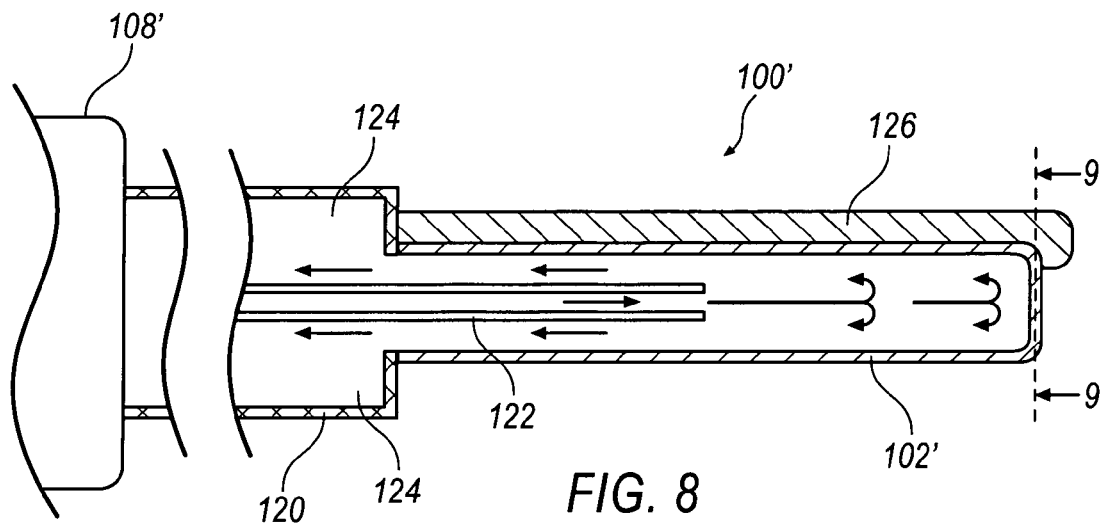
FIG. 8 is a cross-sectional view of a cryo-ablation treatment device for use with the treatment device wand of FIG. 7.
Figure 9:
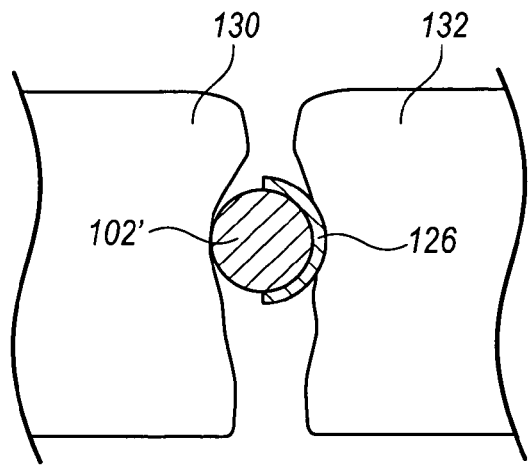
FIG. 9 is a cross-sectional view of the cryo-ablation treatment device of FIG. 8 as used in a medical procedure.

An alternative embodiment of treatment device 100' is depicted in FIG. 8. Treatment device 100' is a cryo-ablation device. Treatment device 100', utilizing cryo-ablation, is a surgical technique using extremely cold temperatures to destroy cells. In the illustrated embodiment, treatment device 100' includes an inner cannula 120 sized to fit within outer cannula 24 of system 20. Treatment tip 102' is sized to extend beyond distal end 38 of outer cannula 24 and directly interface the patient's tissue. A supply tube 122 extends from treatment handpiece 108' through inner cannula 120 and provides freezing liquid to treatment tip 102'. The freezing liquid exits treatment tip 102' through a return cavity 124 defined as a region between inner cannula 120 and supply tube 122. Treatment tip 102' is configured to directly interface the patient's tissue and deliver the freezing treatment to the tissue surrounding treatment tip 102'.

Additionally, treatment tip 102' may include a shield 126 that allows for a portion of the tissue surrounding treatment tip 102' to be substantially protected from the freezing treatment. Thus, a surgeon may use shield 126 in sensitive areas so that undesired damage does not occur to sensitive tissues. For example, as illustrated in more detail in FIG. 9, treatment tip 102' is used between a target tissue 130 and a protected tissue 132. In this example, a surgeon may intend target tissue 130 to receive the cryo-ablation from treatment tip 102'. However, a sensitive tissue, such as an intestinal wall or skin, may not be able to withstand the treatment. In the case of an intestinal wall, the freezing may create an opening that may cause leakage and infection. Similarly, the skin may become damaged and a breaking of the skin may result. In these cases, shield 126 insulates protected tissue 132 from the freezing effects.

Figure 10:
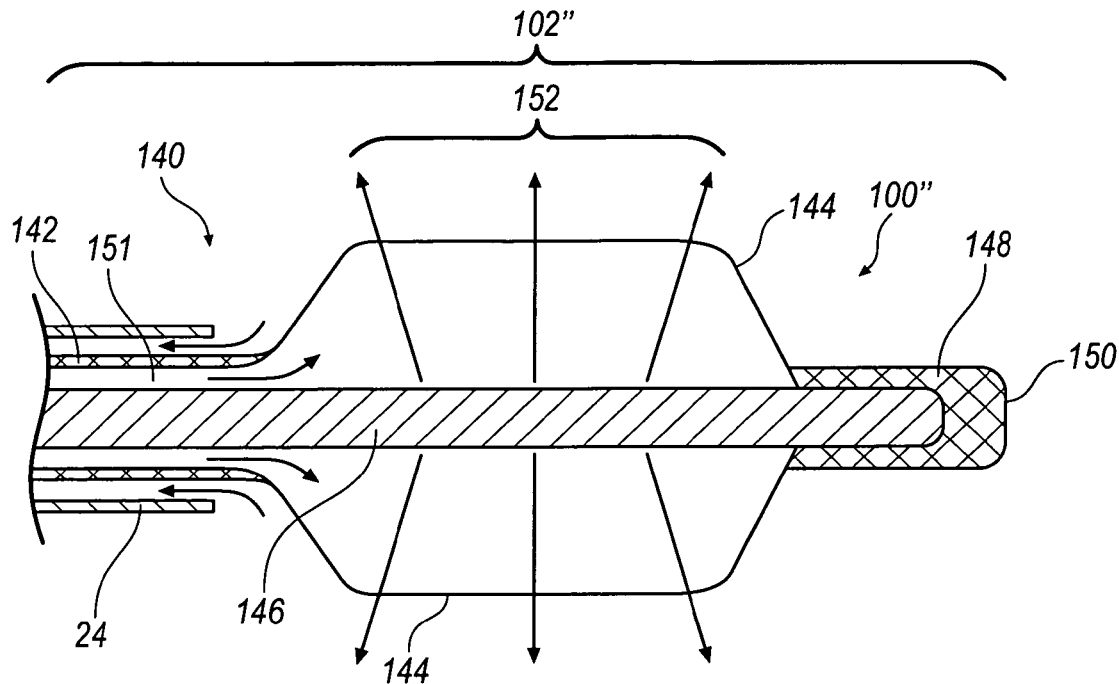
FIG. 10 is a cross sectional view of a photodynamic treatment device for use with the treatment device wand of FIG. 7.

Another alternative embodiment of treatment device 100'' having treatment tip 102'' is embodied as a photodynamic treatment device 140 as illustrated in FIG. 10. Photodynamic treatment device 140 includes a support shaft 142 sized to fit within outer cannula 24 of system 20, a balloon 144 configured for inflation when extended beyond outer cannula 24 of system 20, an optic guide 146 configured to deliver light, and a cap 148 configured to secure balloon 144 and optic guide 146 at a distal end 150. Photodynamic treatment device 140 utilizes a light source and, if desired, a photosensitizing agent to effectuate destruction of tissue at a desired location.

In operation, balloon 144 is inflated by a high pressure provided by an inflation channel 151 positioned between optic guide 146 and support shaft 142. Once inflated, balloon 144 is pressed against the surrounding tissue and a high power light source is activated. Photodynamic treatment device 140 then provides emitted light 152 to the treatment location. The heating effects of emitted light 152 may alone be sufficient for treatment. However, if desired, a photosensitizing agent may be applied to the treatment location to improve the destructive effect of emitted light 152. The photosensitizing agent may be applied before the surgical procedure, or alternatively, be applied locally by wand 68. When a photosensitizing agent is used, emitted light 152 interacts with the agent providing enhanced tissue destruction. Further, the photosensitizing agent may be configured to have an affinity for cancerous cells. Thus, damage to healthy tissues is further reduced.

Figure 11:
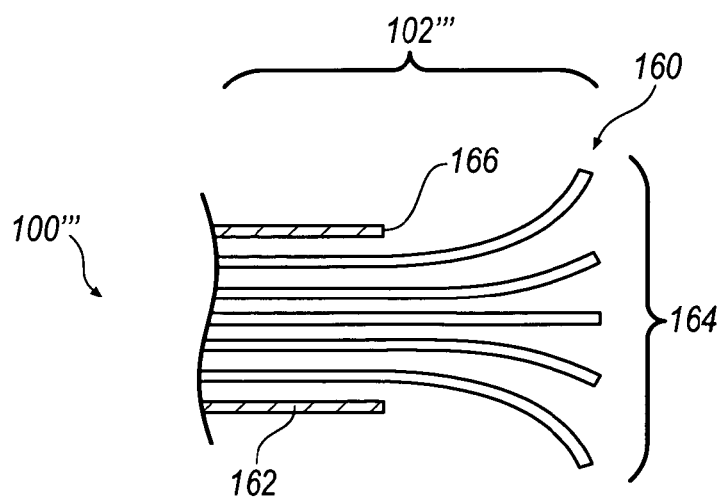
FIG. 11 is a side view of a radiofrequency treatment device for use with the treatment device wand of FIG. 7.

Another alternative embodiment of treatment device 100''' having treatment tip 102''' is a radiofrequency ablation device 160 as illustrated in FIG. 11. Radiofrequency ablation device 160 includes a delivery cannula 162 sized to fit within outer cannula 24 of system 20 and one or more probes 164 configured to deliver radiofrequency energy to surrounding tissue. When inserting delivery cannula 162 in outer cannula 24 of system 20, probes 164 are retracted within delivery cannula 162. After reaching the appropriate depth to access the treatment location, probes 164 are extended beyond a distal end 166 of delivery cannula 162. After extension, probes 164 are in communication with the surrounding tissue and may be energized to effectuate treatment.

Yet another alternative embodiment of treatment device 100 includes a laser ablation device that utilizes heat to ablate tissue.

Still another alternative embodiment of treatment device 100 includes the use of localized interstial brachytherapy. In using this approach, a radioactive substance is provided interstially via balloon systems, one or more radioactive seeds, or the like, which may be placed (either temporarily or permanently) at the suspect tissue.

Referring to FIGS. 12-21, a medical procedure of the present invention will be described. In one embodiment, system 20 is employed to provide adjuvant treatment of a target tissue 80 within a patient's body 170. Target tissue 80, or lesion, to be biopsied and/or removed and subsequently adjuvantly treated is located using a medical imaging system, such as MRI or other suitable imaging modalities. A reference structure 172 may be positioned adjacent patient's body 170 to assist in locating the target tissue 80. The location of target tissue 80 relative to reference structure 172 may be determined along one or more axes. In the illustrated embodiment, the location of target tissue 80 relative to reference structure 172 is determined along the X and Y axes; however, the target tissue 80 location may also be determined along all three of the X, Y, and Z axes. While the described method employs reference structure 172 to locate target tissue 80, reference structure 172 is not necessarily required and a more "freehand" approach may be utilized.

In an embodiment, reference structure 172 includes a support grid having a number of holes therethrough. Each hole is sized to allow passage of outer cannula 24. The hole through which outer cannula 24 is ultimately inserted is determined by the location of target tissue 80 relative to reference structure 172 along the X and Y axes. Patient's body 170 and reference structure 172 are viewed using a medical imaging system, such as MRI, to determine the location of target tissue 80 relative to reference structure 172.

Figure 12:
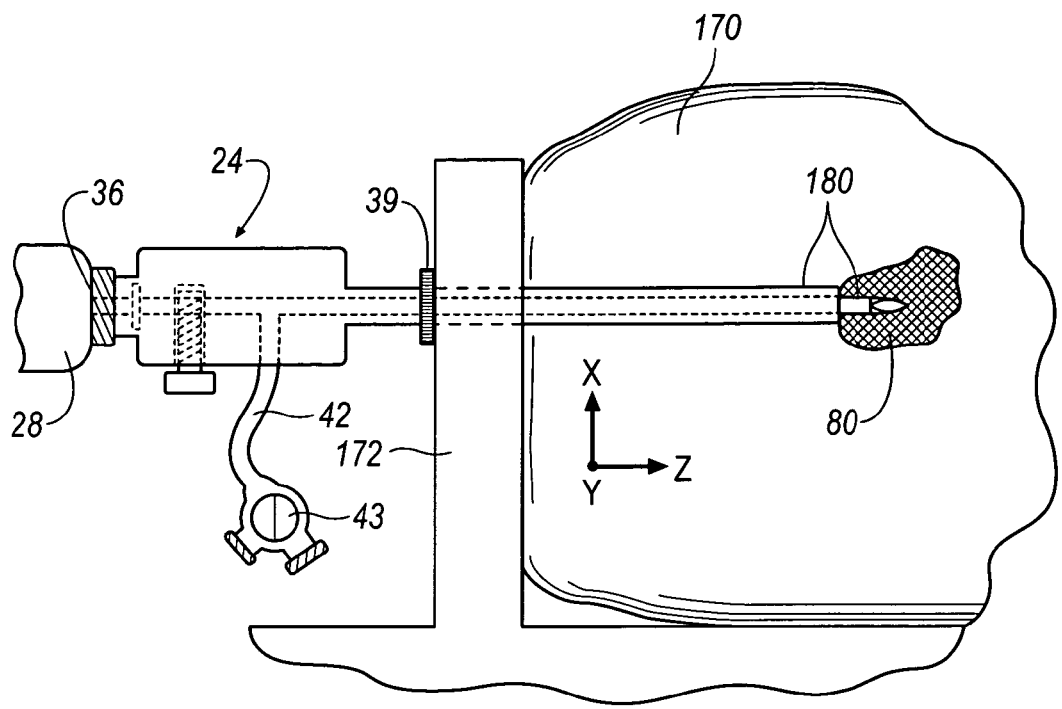
FIGS. 12-21 are elevational views illustrating different stages of a medical procedure using the medical system of the present invention.

After application of anesthesia, the stylet portion of introducer stylet 22 and a portion of outer cannula 24 are inserted through the support grid and into patient's body 170, creating a pathway 180 to target tissue 80 (see, e.g., FIG. 12). Introducer stylet 22 is then removed from patient's body 170 leaving behind outer cannula 24 and pathway 180 (see, e.g., FIG. 13).

Fluids may be inserted into or removed from patient's body 170 through inner lumen 40 via fluid conduit 42. These fluids may include, for example, additional anesthetics and/or saline solution to cleanse pathway 180 and remove blood. Accumulated blood and other fluids within pathway 180 may be aspirated through fluid conduit 42 or by inserting wand 68 prior to insertion of target confirmation device 26, 26', 26".

Figure 13:
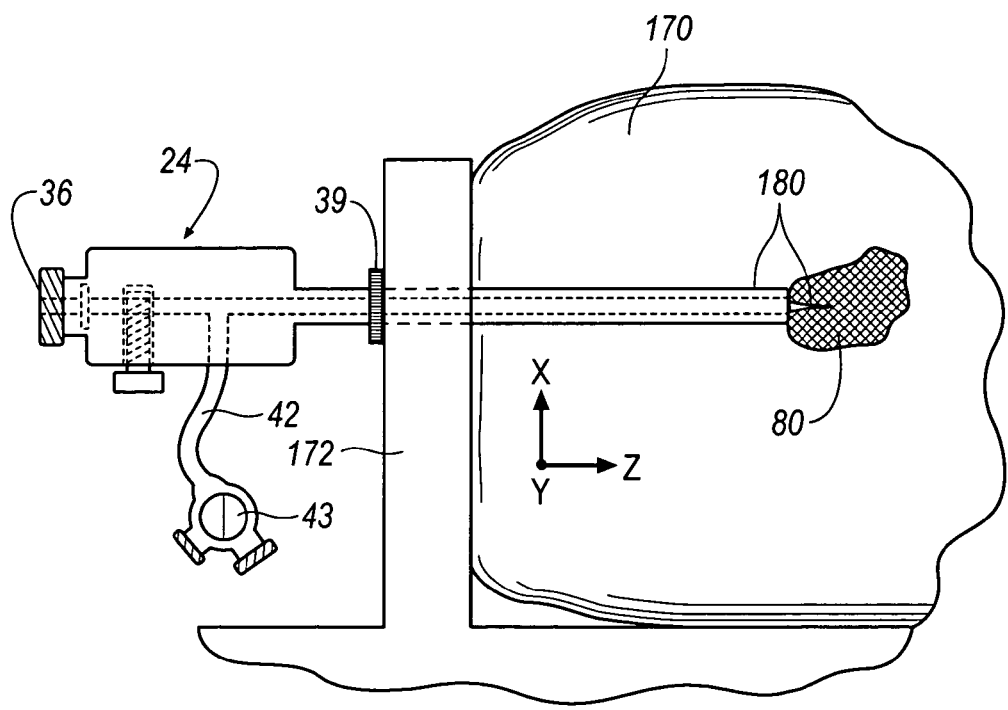
Figure 14:
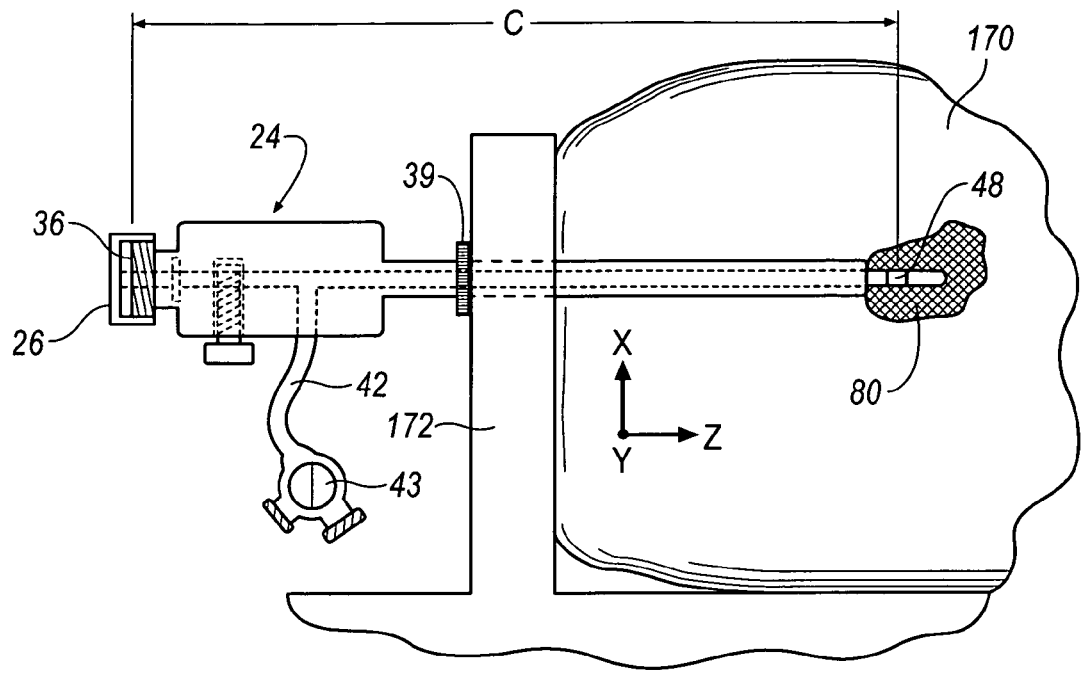

Once introducer stylet 22 is removed from outer cannula 24, target confirmation device 26, 26', 26" may be inserted into patient's body 170 through the path 180 created by outer cannula 24 (see, e.g., FIGS. 13 and 14). With target confirmation device 26, 26', 26" properly inserted into outer cannula 24, an image of the target site is again taken to determine the location of targeting band 48 or distal end 46', 46" in relation to target tissue 80 and reference structure 172. If targeting band 48 or distal end 46', 46" is in the desired position adjacent target tissue 80 along the Z-axis, target confirmation device 26, 26', 26" is removed from outer cannula 24. However, if targeting band 48 or distal end 46', 46" is not in the desired position, then the position of target confirmation device 26, 26', 26" and outer cannula 24 is modified along the Z-axis until the desired position is achieved.

Once the desired position is achieved, depth limiting member 39 is moved against reference structure 172 to inhibit movement of outer cannula 24 further into patient's body 170. When no reference structure 172 is used, depth limiting member may be moved directly against the patient's skin. Target confirmation device 26, 26', 26" is then removed from outer cannula 24 and resection apparatus 50 is inserted into outer cannula 24 until handpiece 54 abuts proximal end 36 of outer cannula 24.

Figure 15:
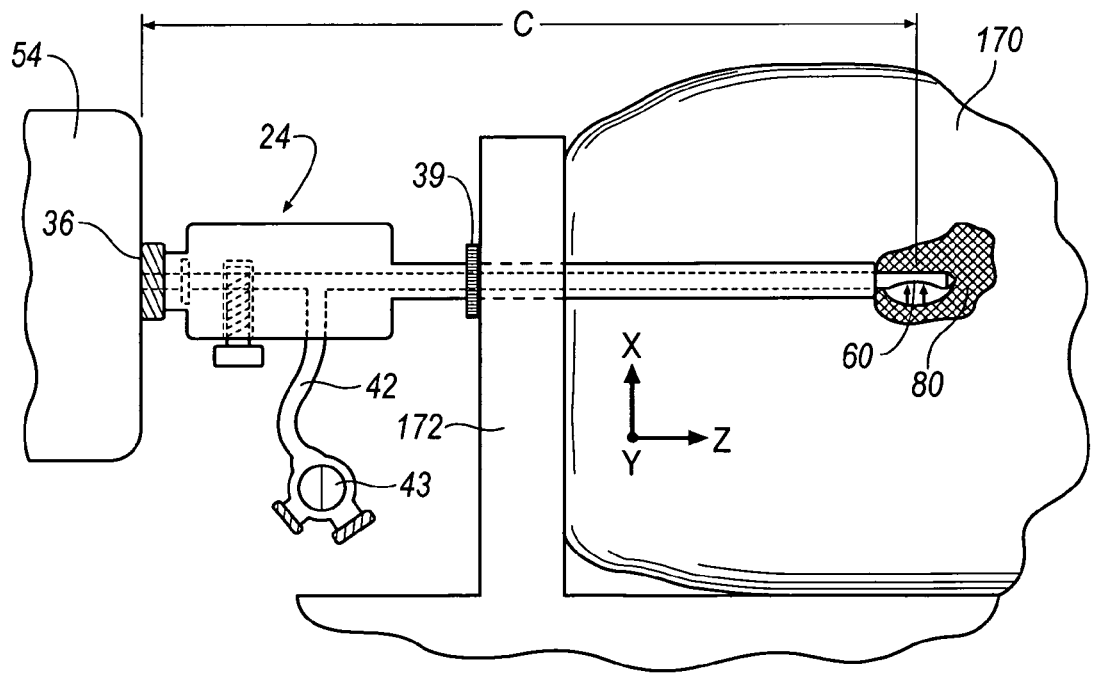

In the embodiment illustrated in FIG. 15, one or more samples of target tissue 80 are removed from patient's body 170 through tissue-receiving opening 60. The correct position of tissue-receiving opening 60 is ensured because the distance "C" between connecting end 44 of target confirmation device 26, 26', 26" and targeting band 48 (see, e.g., FIGS. 3 and 14), or the distance between connecting end 44 and the predetermined location on target confirmation device 26, 26', 26" (FIGS. 3, 3A, 3B), is approximately equal to the distance between the center of tissue-receiving opening 60 and handpiece 54 of resection apparatus 50.

Figure 16:
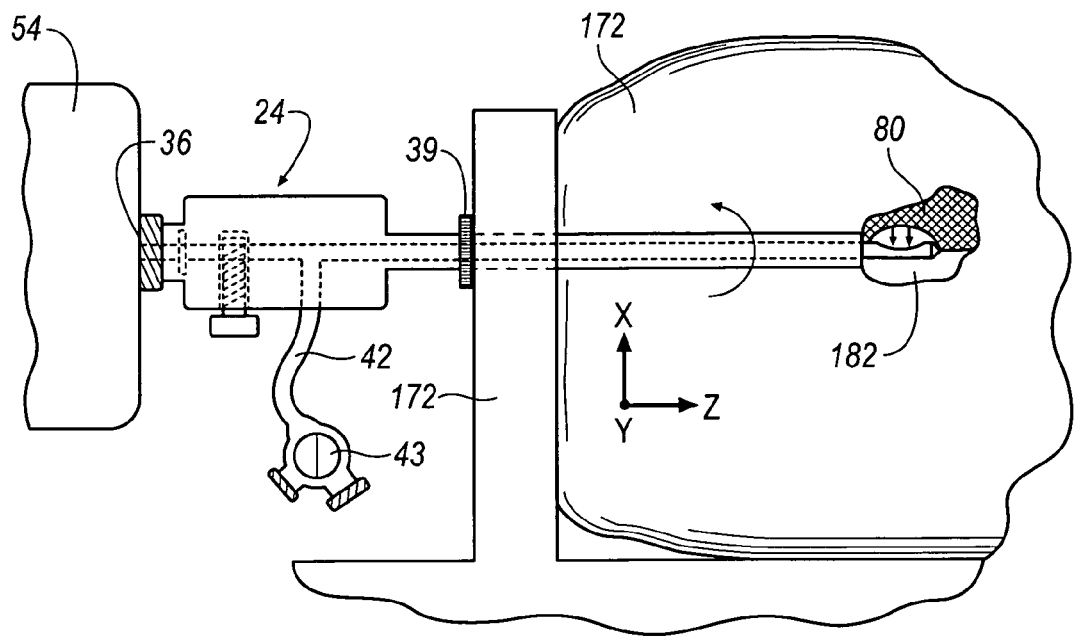

FIG. 16 illustrates the use of resection apparatus 50 for debulking a region of tissue where target tissue 80 is a significant region. In this case, resection apparatus 50 may be rotated and used to debulk the entire region of target tissue 80. As illustrated, resection apparatus 50 has been rotated leaving a void 182 and is used to resect the remaining portion of target tissue 80.

Generally, the debulking procedure may be used where suspicion of cancerous tissue exists, or where treatment of a previously resected region is desired. In the case where a biopsy has previously been taken, the debulking process removes any hematomas that may have developed due to the biopsy or earlier procedure. In addition to resection of suspect tissues, removal of fluids and hematomas improves the efficacy of the adjuvant treatment because any fluids or hematomas act as insulators to adjuvant treatment such as cryoablation and reduce the effectiveness of the freezing penetration.

Figure 17:
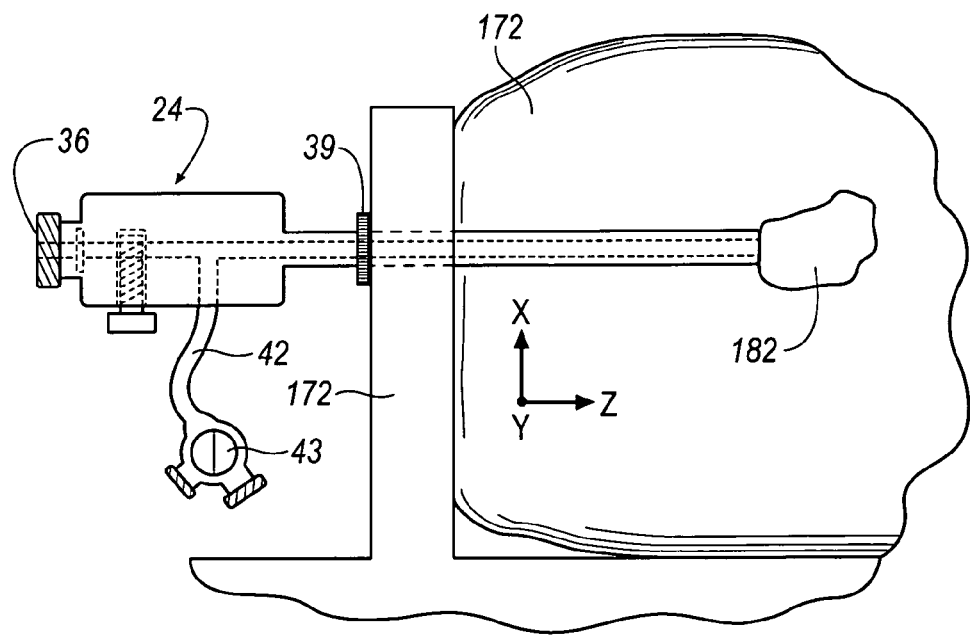
Figure 18:
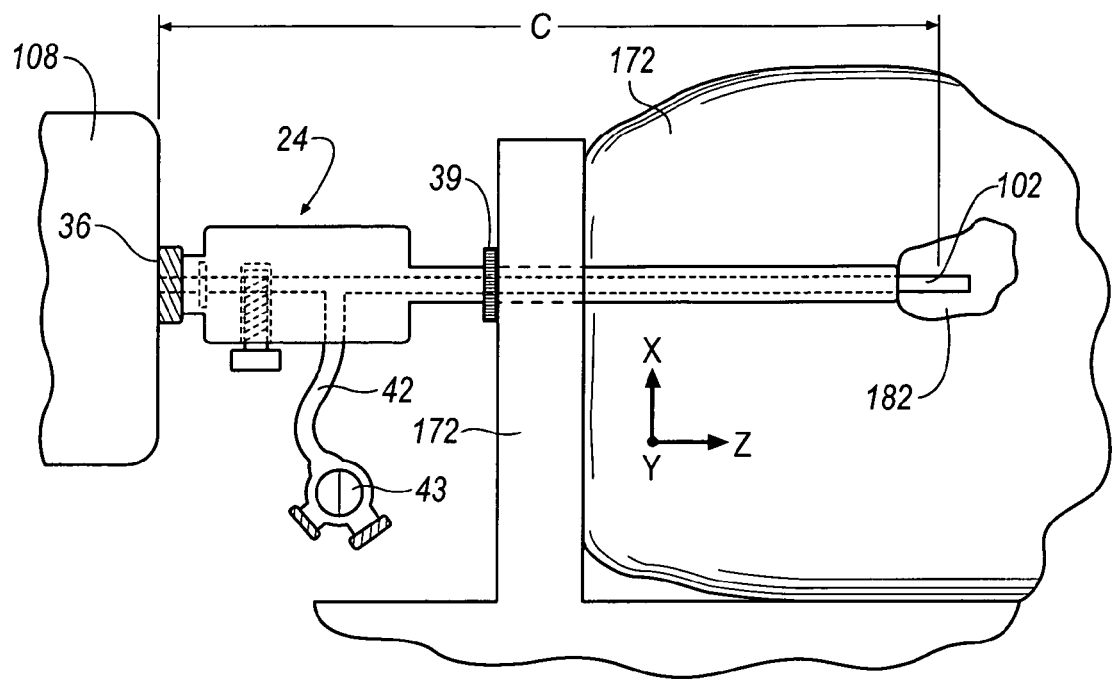

When resection of target tissue 80 is complete, resection apparatus 50 is removed from patient's body 170 leaving void 182 (see, e.g., FIG. 17). Treatment device 100, 100', 100", 100''' may then be inserted into patient's body 170 through outer cannula 24 (see, e.g., FIGS. 7 and 18). Treatment tip 102, 102', 102", 102''' is correctly positioned within void 182 because the distance "C" between connecting end 44 of target confirmation device 26, 26', 26" and targeting band 48 or distal end 46', 46" (see, e.g., FIGS. 3 and 14) is approximately equal to the distance between the center of tissue-receiving opening 60 and handpiece 54 of resection apparatus 50, and is approximately equal to the distance between a predetermined portion of treatment tip 102, 102', 102", 102''' and treatment handpiece 108 of treatment device 100, 100', 100", 100''' (FIG. 7).

Figure 19A:
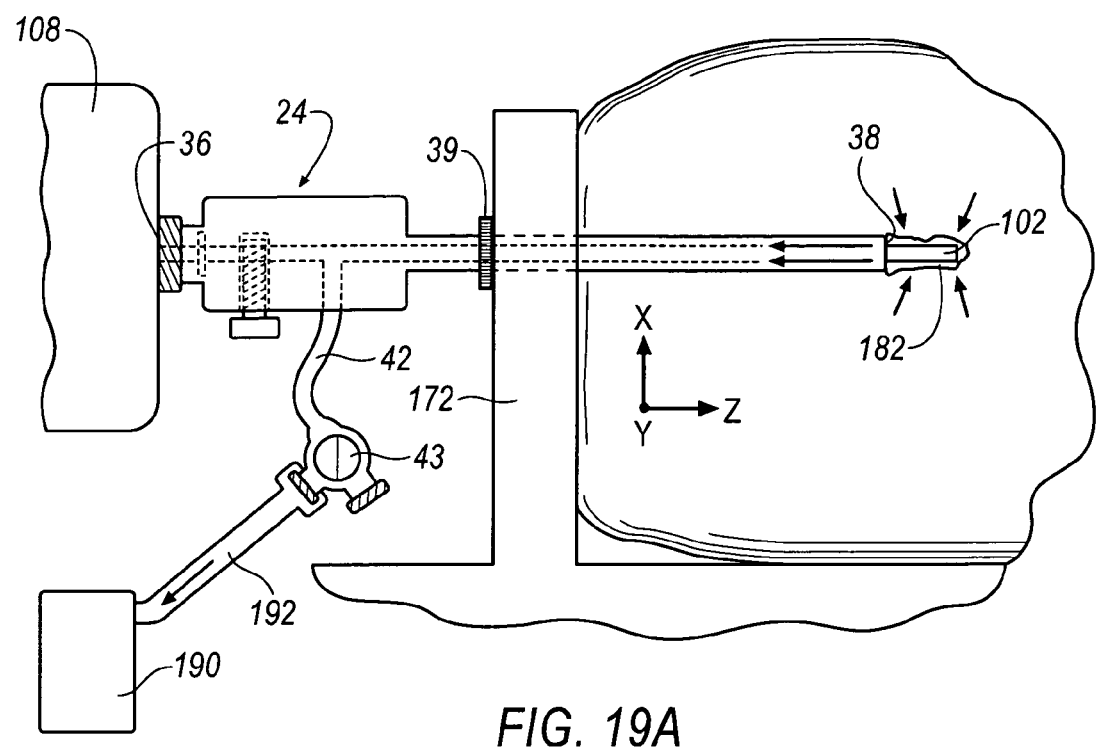
Figure 19B:
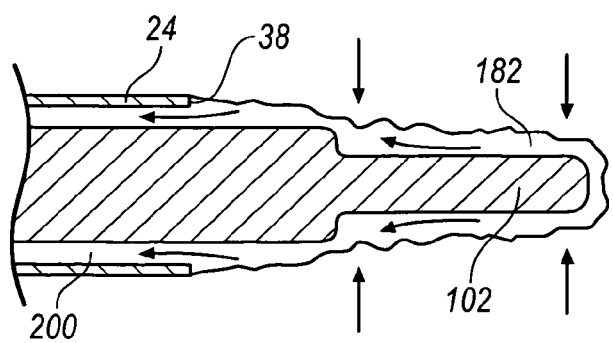

With treatment device 100, 100', 100", 100''' inserted into patient's body 170 (see FIG. 18), a vacuum device 190 may be attached to fluid conduit 42 by a vacuum hose 192 (see FIG. 19A). A surgeon may then operate vacuum device 190 to create a vacuum though lumen 40 of outer cannula 24. The vacuum through lumen 40 draws tissue close to open distal end 38 and collapses void 182 around treatment tip 102, 102', 102", 102'''. FIG. 19B illustrates the collapsing of void 182 around treatment tip 102, 102', 102", 102'''. A gap 200 between treatment tip 102, 102', 102", 102''' and outer cannula 24 provides a path for the vacuum to collapse void 182.

Figure 20A:
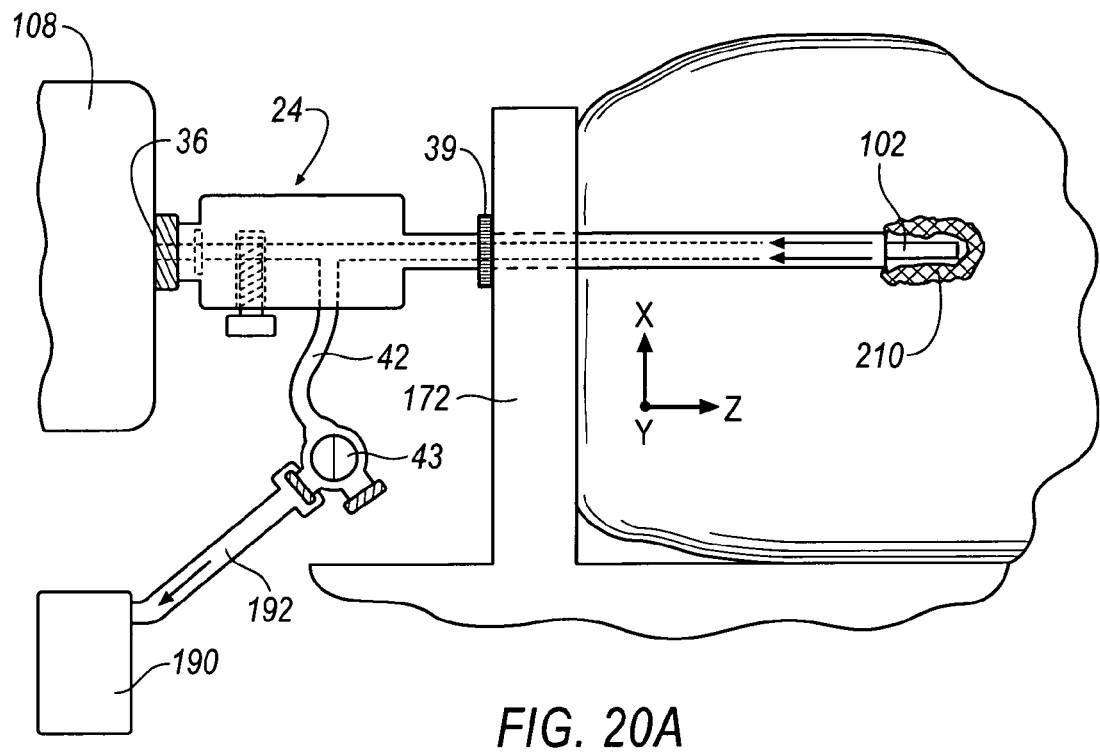
Figure 20B:
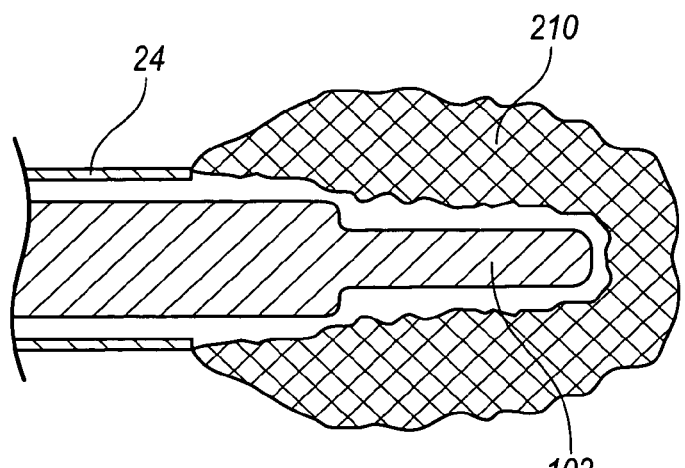
Figure 21:
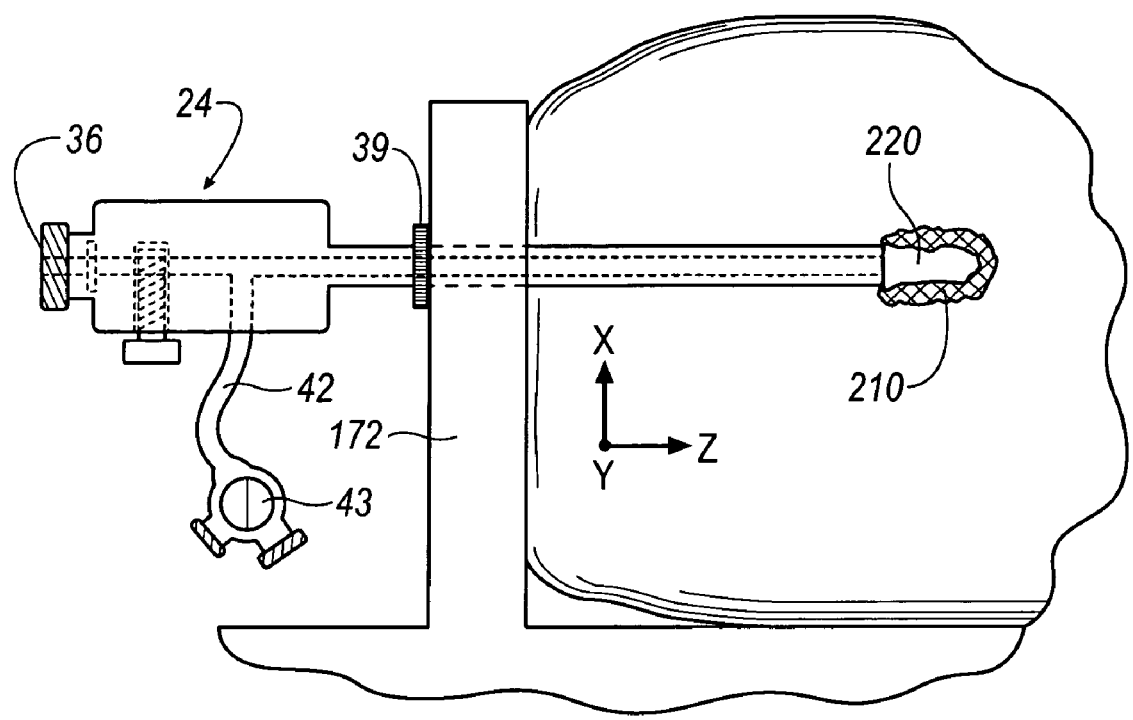

Once void 182 has collapsed under the vacuum, treatment tip 102, 102', 102", 102''' is activated (see FIG. 20A). The resulting damage to the surrounding tissue creates a margin 210 of ablated tissue that results in an increased success rate for treatment. FIG. 20B illustrates in detail margin 210 surrounding treatment tip 102, 102', 102", 102''' after the adjuvant treatment has been applied. The cells in margin 210 have been ablated and no longer pose a threat of continued growth of cancerous cells that may have been interstially surrounding target tissue 80.

After the adjuvant treatment has been applied, the surgeon may remove treatment device 100, 100', 100", 100'''. Depending upon the type of adjuvant treatment applied through treatment tip 102, 102', 102", 102''', a post-treatment void may remain even after treatment device 100, 100', 100", 100''' is removed from patient's body 170. The surgeon may then review margin 210 under a preferred imaging modality. If, for example, it is determined that the margin is not correctly positioned or the adjuvant treatment has not achieved the appropriate margin 210, treatment may be continued by applying the adjuvant treatment repeatedly until medical imaging satisfactorily verifies the margin. Alternatively, margin 210 may be improved by repeating the procedure or a portion of the procedure beginning from any step. Further, the procedure may be repeated a predetermined number of times in order to reach an effective margin depth or shape.

After completion of the procedure, void 182 may be aspirated using wand 68. During or after aspiration, if any aspiration is desired, a final image of margin 210 may be taken to confirm removal of target tissue 80. The imaging also provides a record of the ablation zone for further analysis. Finally, an MRI identifiable treatment site marker, a collagen plug, or other medical treatment may be inserted into the biopsy site through outer cannula 24.

Among other features, the medical system of the present invention localizes the target site in a manner that provides for confirmation of the target site under MRI or other visualization modality, and allows positioning of a resection device to ensure the cutting element of the resection device can be accurately placed at the target site. Further, the medical system provides for accurate positioning of an adjuvant therapy device. Additionally, the system provides for verification of a margin created by an adjunctive therapy.

The medical system of the present invention also reduces side effects related to cancer treatments. Because the system uses accurate targeted treatment of the target site, the overall time the time of treatment is significantly reduced as compared with traditional radiation therapy. Further, there is no widespread exposure to radiation.

While the method is preferably suited for treatment of cancerous tissues that are unifocal, the treatment apparatus and method described herein may be used for any type of treatment including, but not limited to, multifocal diseases.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A system for treating a lesion site of a patient, comprising:
   a cannula having a lumen;
   a conduit in communication with said lumen;
   an introducer stylet removably disposed within said cannula;
   a resecting device selectively insertable within said cannula; and
   an adjuvant treatment device selectively insertable within said cannula, wherein the adjuvant treatment device includes a shield covering a portion of said adjuvant treatment device for protecting a non-targeted tissue region, and a first exterior region and a second exterior region diametrically opposite said first exterior region, said first exterior region and said second exterior region arranged at a common axial location along said adjuvant treatment device, said shield extending over said first exterior region and not over said second exterior region, and wherein at least a portion of the shield is selectively insertable within said cannula;
   wherein the resecting device is a separate component from the adjuvant treatment device.

2. The system of claim 1, further comprising:
   a limiting member configured to limit penetration of said cannula within said patient.

3. The system of claim 2, wherein said limiting member is arranged outside of said cannula and includes an exterior surface for selectively contacting one of said patient's skin and a reference structure for controlling said position of said cannula within said patient.

4. The system of claim 3, wherein said limiting member engages an exterior surface of said cannula.

5. The system of claim 1, further comprising:
   a vacuum passage positioned between said lumen and said adjuvant treatment device, said vacuum passage at least partially defined by an inner surface of said lumen and an outer surface of said adjuvant treatment device.

6. The system of claim 1, further including a vacuum device for creating a vacuum, wherein said vacuum applied to said conduit causes a tissue cavity to collapse upon said adjuvant treatment device.

7. The system of claim 1, wherein said adjuvant treatment device operates using at least one of cryo-ablation, radiofrequency-ablation, heating, brachytherapy, and photodynamic therapy.

8. The system of claim 1, further comprising:
   a target confirmation device selectively insertable within the cannula.

9. The system of claim 1, wherein said lumen includes an open proximal end through which said introducer stylet, said resecting device and said adjuvant treatment device are inserted into and removed from said cannula, and an opposite distal end, said system further comprising a valve fluidly connected to said lumen, said valve selectively moveable between an open position for establishing a fluid path between said distal and proximal ends of said lumen, and a closed position for substantially fluidly blocking said fluid path between said distal and proximal ends of said lumen.

10. An adjuvant therapy system for a lesion site, comprising:
    a cannula having a lumen;
    a port in communication with said lumen;
    a limiting member moveably connected to said cannula and configured to position said cannula within said patient;
    a reference structure configured to selectively engage said limiting member, said reference structure including at least one aperture for slidably receiving said cannula;
    an introducer stylet selectively and removably disposed within said cannula;
    a debulking device selectively insertable within said cannula, said debulking device configured for removing tissue from said lesion site;
    an adjuvant treatment device selectively insertable within said cannula for treating the lesion site, wherein the debulking device is a separate component from the adjuvant treatment device; and
    a vacuum source operably connected to said port, wherein said vacuum source causes a tissue cavity to collapse upon said adjuvant treatment device.

11. The adjuvant therapy system of claim 10, further comprising:
    a target confirmation device selectively insertable within said cannula.

12. The adjuvant therapy system of claim 10, wherein said adjuvant treatment device utilizes at least one of cryo-ablation, radiofrequency-ablation, heating, and photodynamic therapy.

13. The adjuvant therapy system of claim 10, wherein a photosensitizing agent is delivered to said lesion site.

14. The adjuvant therapy system of claim 13, wherein said adjuvant treatment device illuminates said lesion site.

15. The adjuvant therapy system of claim 10, wherein said limiting member is arranged outside of said cannula and includes an exterior surface for selectively contacting one of said patient's skin and a reference structure to control said position of said cannula within said patient.

16. The adjuvant therapy system of claim 15, wherein said limiting member engages an exterior surface of said cannula.

17. The adjuvant therapy system of claim 10, wherein said lumen includes an open proximal end through which said introducer stylet, said resecting device and said adjuvant treatment device are inserted into and removed from said cannula, and an opposite distal end, said adjuvant therapy system further comprising a valve fluidly connected to said lumen, said valve selectively moveable between an open position for establishing a fluid path between said distal and proximal ends of said lumen, and a closed position for substantially fluidly blocking said fluid path between said distal and proximal ends of said lumen.

18. The system of claim 17, wherein said valve is arranged along said fluid path between said port and said proximal end of said lumen.

19. A surgical treatment apparatus comprising:

a cryo-ablation probe having a distal end, and a first exterior region and a second exterior region diametrically opposite said first exterior region, said first exterior region and said second exterior region arranged at a common axial location along said adjuvant treatment device, wherein said distal end is insertable at least partially through a cannula and ablates a first tissue when located adjacent said first exterior region; and a shield extending over said first exterior region for protecting a second tissue and not extending over said second exterior region, said shield insertable at least partially through the cannula.

20. The apparatus of claim 19, wherein said shield is partially constructed from at least one of plastic, rubber, or PTFE.

* * * * *